(12) United States Patent
Park et al.

(10) Patent No.: US 12,352,961 B2
(45) Date of Patent: Jul. 8, 2025

(54) PROTECTION OF USER'S HEALTH FROM OVERINDULGENCE IN METAVERSE

(71) Applicant: QUALCOMM Incorporated, San Diego, CA (US)

(72) Inventors: Sunwoo Park, Yongin-si (KR); Justin Mcgloin, Los Altos, CA (US); Heegyum Kim, Bucheon-si (KR); Won-Seon Choi, Seoul (KR)

(73) Assignee: QUALCOMM Incorporated, San Diego, CA (US)

( * ) Notice: Subject to any disclaimer, the term of this patent is extended or adjusted under 35 U.S.C. 154(b) by 340 days.

(21) Appl. No.: 17/808,698

(22) Filed: Jun. 24, 2022

(65) Prior Publication Data

US 2023/0418061 A1 Dec. 28, 2023

(51) Int. Cl.
*G02B 27/01* (2006.01)
*A61B 5/00* (2006.01)
*G06F 3/04815* (2022.01)

(52) U.S. Cl.
CPC ........ *G02B 27/0149* (2013.01); *A61B 5/7275* (2013.01); *G06F 3/04815* (2013.01); *G02B 2027/0167* (2013.01)

(58) Field of Classification Search
CPC ... A61B 2562/0219; A61B 5/01; A61B 5/021; A61B 5/02416; A61B 5/02438; A61B 5/1118; A61B 5/1123; A61B 5/14551; A61B 5/6803; A61B 5/6814; A61B 5/6825; A61B 5/6829; A61B 5/7275; A61B 5/7282; A61B 5/746; G02B 2027/0167; G02B 27/0149; G06F 3/011; G06F 3/015; G06F 3/016; G06F 3/04815; G09B 5/06

See application file for complete search history.

(56) References Cited

U.S. PATENT DOCUMENTS

| | | | |
|---|---|---|---|
| 2018/0260026 A1 | 9/2018 | Drake et al. | |
| 2019/0388175 A1* | 12/2019 | Tatsuta | A61B 1/06 |
| 2019/0394437 A1* | 12/2019 | Ryu | H04N 9/646 |
| 2020/0214647 A1 | 7/2020 | Peng et al. | |
| 2021/0399911 A1* | 12/2021 | Jorasch | H04L 12/1818 |
| 2022/0062621 A1* | 3/2022 | Hogg | A61N 1/36014 |
| 2022/0139554 A1* | 5/2022 | Pillay | G16H 70/20 |
| | | | 705/2 |

OTHER PUBLICATIONS

International Search Report and Written Opinion—PCT/US2023/020473—ISA/EPO—Aug. 1, 2023.

* cited by examiner

*Primary Examiner* — Ming Wu
(74) *Attorney, Agent, or Firm* — QUALCOMM Incorporated

(57) ABSTRACT

Innovative techniques and apparatuses to control metaverse presentation are disclosed. The proposed techniques and apparatuses allow prevention of overindulgence to metaverse presentation based on user biometrics (e.g., oxygen saturation, heart rate, body temperature, blood pressure, etc.). If the biometrics indicate that the user's health is compromised due to the metaverse presentation, the metaverse presentation (visual, audio, haptic outputs) may be altered to reduce the user's overindulgence.

40 Claims, 9 Drawing Sheets

PROTECTION OF USER'S HEALTH FROM OVERINDULGENCE IN METAVERSE

FIELD OF DISCLOSURE

This disclosure relates generally to apparatus and method for protection of user's health from overindulgence in metaverse.

BACKGROUND

Metaverse focuses on close connection between physical and virtual reality. It is typically not immersed in virtual spaces that are far from reality. Rather, metaverse expands the existence into another space connected to reality in someway. Metaverse space will typically include element such as augmented reality (AR), virtual reality (VR), gaming, commerce, and social networking. As technology progresses, the metaverse presentation can become very realistic.

Overindulgence in metaverse can be problematic including causing health problems. For example, violent sports games in metaverse (e.g., boxing, martial arts, etc.) can increase the likelihood of causing problems. Unfortunately, there is little to no countermeasures to combat such overindulgence.

Accordingly, there is a need for systems, apparatus, and methods that overcome the deficiencies of conventional devices including the methods, system and apparatus provided herein.

SUMMARY

The following presents a simplified summary relating to one or more aspects and/or examples associated with the apparatus and methods disclosed herein. As such, the following summary should not be considered an extensive overview relating to all contemplated aspects and/or examples, nor should the following summary be regarded to identify key or critical elements relating to all contemplated aspects and/or examples or to delineate the scope associated with any particular aspect and/or example. Accordingly, the following summary has the sole purpose to present certain concepts relating to one or more aspects and/or examples relating to the apparatus and methods disclosed herein in a simplified form to precede the detailed description presented below.

An exemplary metaverse controller is disclosed. The metaverse controller may comprise a user condition determiner configured to determine a user condition based on biometrics of a user sensed by one or more biometric sensors. The metaverse controller may also comprise a presentation controller configured to control one or more metaverse outputs of a metaverse presentation based on the user condition. The metaverse outputs may comprise any one or more of a visual output, an audio output, and a haptic output. The metaverse presentation may comprise a presentation that incorporates extended reality (XR).

A method of controlling a metaverse presentation is disclosed. The method may comprise determining a user condition based on biometrics of a user sensed by one or more biometric sensors. The method may also comprise controlling one or more metaverse outputs of a metaverse presentation based on the user condition. The metaverse outputs may comprise any one or more of a visual output, an audio output, and a haptic output. The metaverse presentation may comprise a presentation that incorporates extended reality (XR).

Another exemplary metaverse controller is disclosed. The metaverse controller may comprise means for determining a user condition based on biometrics of a user sensed by one or more biometric sensors. The metaverse controller may also comprise means for controlling one or more metaverse outputs of a metaverse presentation based on the user condition. The metaverse outputs may comprise any one or more of a visual output, an audio output, and a haptic output. The metaverse presentation may comprise a presentation that incorporates extended reality (XR).

A non-transitory computer-readable medium storing computer-executable instructions for a metaverse controller comprising one or more processors communicatively coupled to one or more memories is disclosed. The computer-executable instructions may comprise one or more instructions instructing the one or more processors to determine a user condition based on biometrics of a user sensed by one or more biometric sensors. The computer-executable instructions may also comprise one or more instructions instructing the one or more processors to control one or more metaverse outputs of a metaverse presentation based on the user condition. The metaverse outputs may comprise any one or more of a visual output, an audio output, and a haptic output. The metaverse presentation may comprise a presentation that incorporates extended reality (XR).

Other features and advantages associated with the apparatus and methods disclosed herein will be apparent to those skilled in the art based on the accompanying drawings and detailed description.

BRIEF DESCRIPTION OF THE DRAWINGS

A more complete appreciation of aspects of the disclosure and many of the attendant advantages thereof will be readily obtained as the same becomes better understood by reference to the following detailed description when considered in connection with the accompanying drawings which are presented solely for illustration and not limitation of the disclosure.

Figure 1A:
FIG. 1A illustrates a superficial temporal artery.

Other objects and advantages associated with the aspects disclosed herein will be apparent to those skilled in the art based on the accompanying drawings and detailed description. In accordance with common practice, the features depicted by the drawings may not be drawn to scale. Accordingly, the dimensions of the depicted features may be arbitrarily expanded or reduced for clarity. In accordance with common practice, some of the drawings are simplified for clarity. Thus, the drawings may not depict all components of a particular apparatus or method. Further, like reference numerals denote like features throughout the specification and figures.

DETAILED DESCRIPTION

Aspects of the present disclosure are illustrated in the following description and related drawings directed to specific embodiments. Alternate aspects or embodiments may be devised without departing from the scope of the teachings herein. Additionally, well-known elements of the illustrative embodiments herein may not be described in detail or may be omitted so as not to obscure the relevant details of the teachings in the present disclosure.

In certain described example implementations, instances are identified where various component structures and portions of operations can be taken from known, conventional techniques, and then arranged in accordance with one or more exemplary embodiments. In such instances, internal details of the known, conventional component structures and/or portions of operations may be omitted to help avoid potential obfuscation of the concepts illustrated in the illustrative embodiments disclosed herein.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

As indicated above, overindulgence in metaverse can be problematic including causing health problems. Mitigation is often left up to the individual users themselves. There are options to allow parents or other care persons or organization to enable mitigation measures. However, these are almost exclusively time based. For example, a parent may allow a child to play for a specific amount of time such as an hour. Thereafter, access to the metaverse device is prohibited. As another example, access may be limited to specific hours of the day such as between 7-9 p.m.

Time-based mitigation does not take the actual level of user's health into account. Thus, to address these and other issues related to metaverse presentation, it is proposed to assess a person's level of exhaustion or stress level to protect a user from overindulgence in metaverse. For example, various biometric sensors may be used to monitor and assess a person's level of exhaustion and/or stress level, and take necessary mitigation steps to prevent overuse and resulting health problems.

Biometric sensors can take many forms. The sensors can be electrical. For example, electrodes (e.g., as used in electrocardiogram (ECG, EKG) to measure electrical signals can be used. Sensors can also be optical. For example, blood oxygen saturation level (SPO2) sensors can be used to measure oxygen level of blood. The biometric sensors can also be a companion device such as a watch.

Figure 1B:
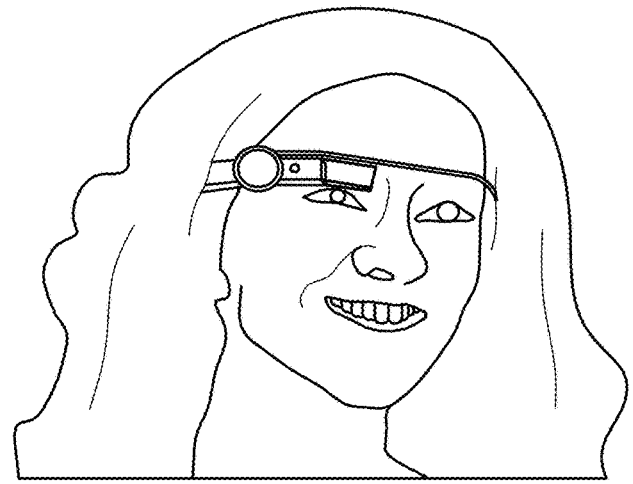
FIGS. 1B and 1C illustrate examples of displays equipped with superficial temporal artery sensors.
Figure 1C:
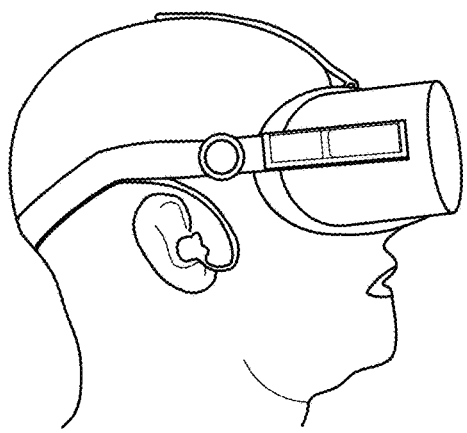

FIG. 1A illustrates a superficial temporal artery, which is an example of an area of a person that can be used to measure biometrics. As seen in FIGS. 1B and 1C, sensor or sensors may be attached to display devices, such as on head mounted displays (HMD), to monitor the superficial temporal artery. Biometrics such as heart rate through photoplethysmography (PPG), temperature, ECG, SPO2, blood pressure, etc. may be measured through a superficial temporal artery sensor. Of course, sensors—electrical and/or optical—can be used to monitor others parts of a person to measure biometrics.

Figure 2A:
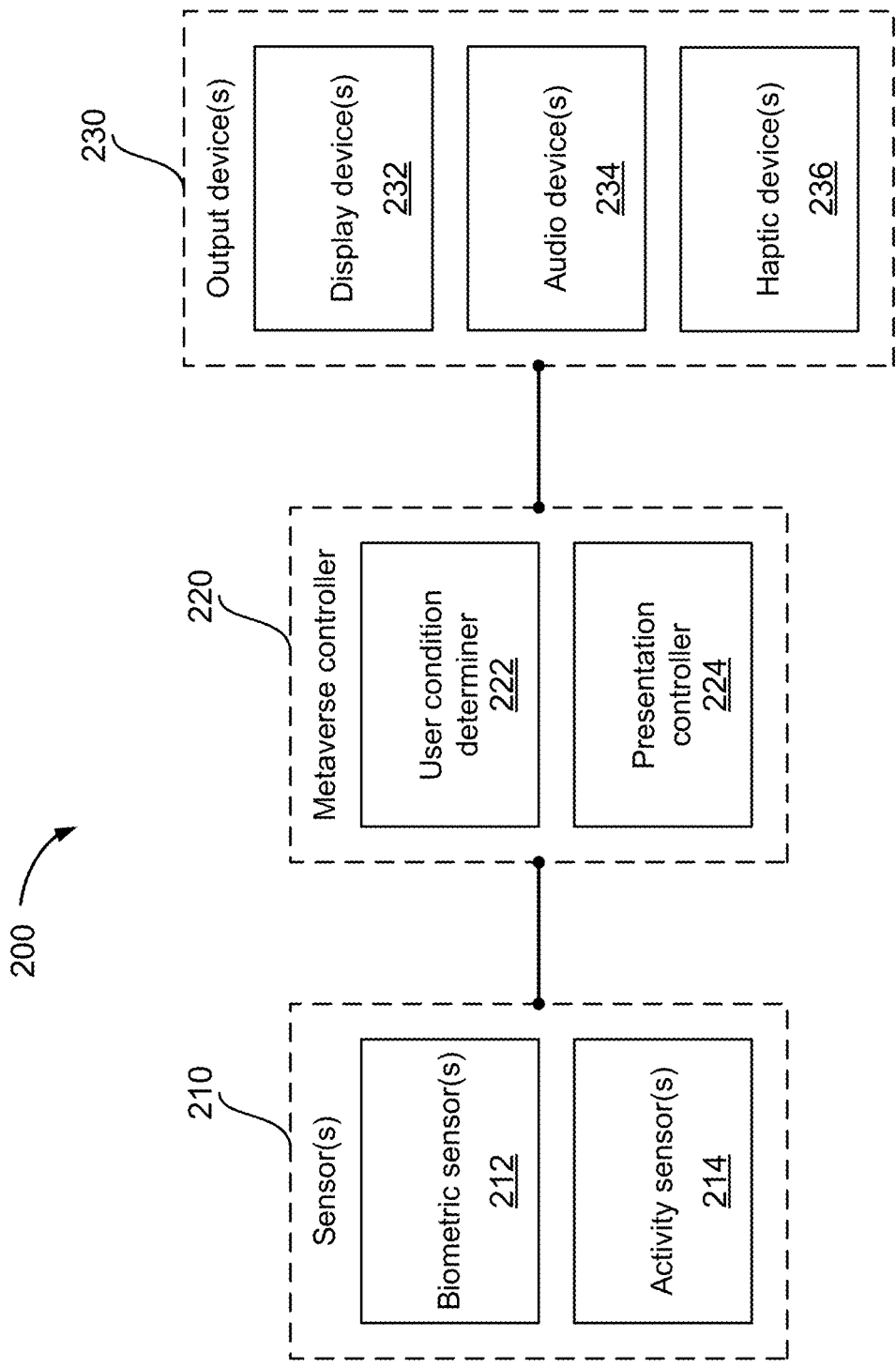
FIGS. 2A and 2B illustrate examples of metaverse presentation systems in accordance with one or more aspects of the disclosure.
Figure 2B:
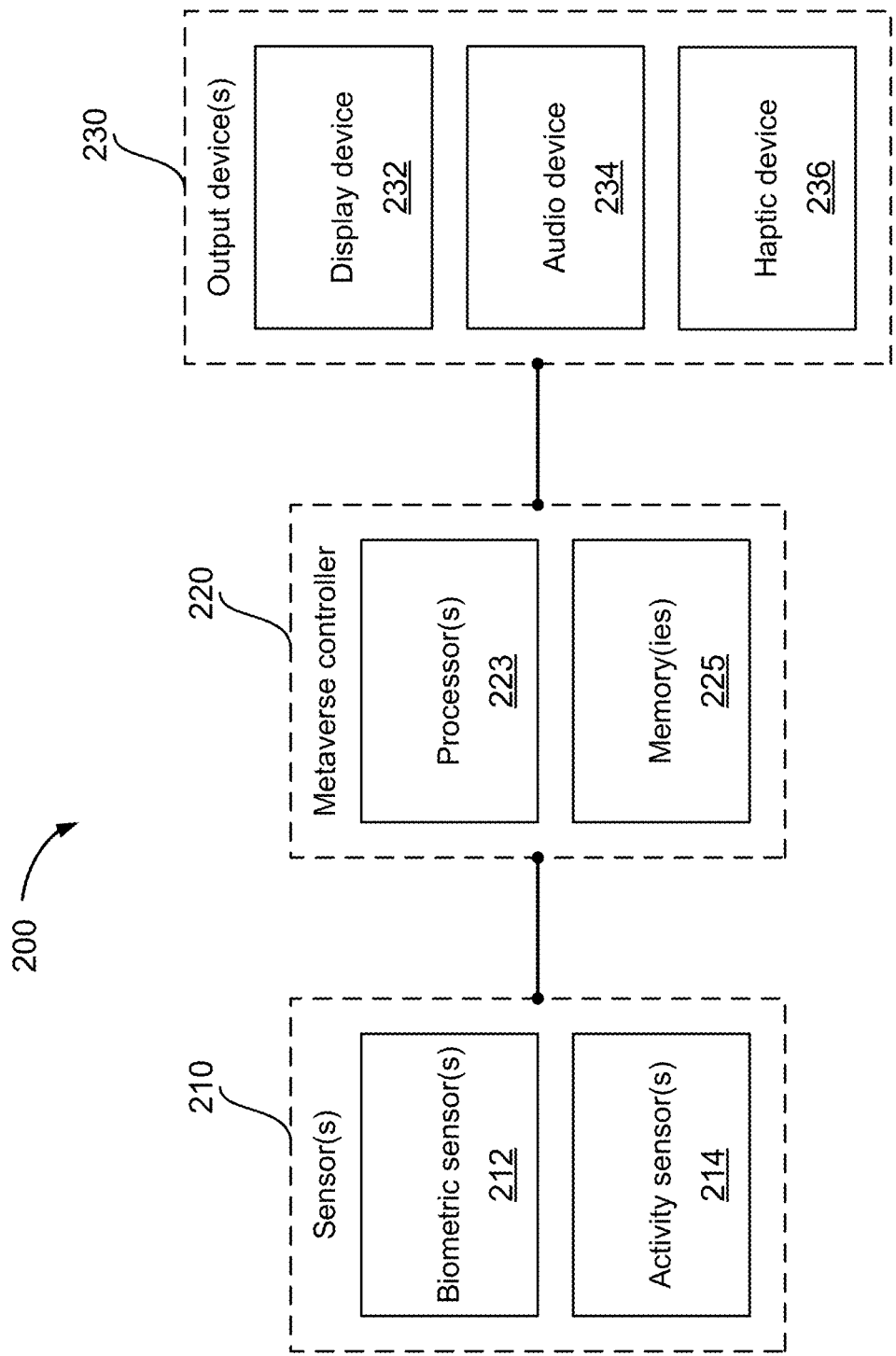

FIGS. 2A and 2B illustrate examples of metaverse presentation systems 200 in accordance with one or more aspects of the disclosure. As indicated above, metaverse presentation can expand existence into another space that is connected to reality in various ways. Such spaces include augmented reality (AR), virtual reality (VR), gaming, commerce, social networking, etc. For ease of description, such spaces may be captured in the phrase "extended reality (XR)". Then it may be said that a metaverse presentation may comprise a presentation that incorporates extended reality.

As seen in FIGS. 2A and 2B, the metaverse presentation system 200 may comprise one or more sensors 210, a metaverse controller 220, and one or more output devices 230. The sensor(s) may include one or more biometric sensors 212. The superficial temporal artery sensor in FIGS. 1B and 1C is an example of a biometric sensor 212. Alternatively or in addition thereto, the biometric sensors 212 may comprise any one or more of electrodes (e.g., for ECG/EKG), SPO2 monitors, PPG sensors, etc. The sensors 210 may also include one or more activity sensors 214, which may be configured to monitor the user physical activity (e.g., sitting, standing, walking, fast walking, jogging, running, sprinting, etc.).

The metaverse controller 220 may be configured to control the outputs of a metaverse presentation, i.e., control the metaverse outputs. The metaverse outputs may comprise any combination of a visual output, an audio output, and a haptic output. Details of the metaverse controller 220 will be described further below.

The one or more output devices 230 may be configured to provide the metaverse presentation based on controls from the metaverse controller 220. The output device(s) 230 may comprise one or more display devices 232 configured to provide the visual output, one or more audio devices 234 configured to provide the audio output, and one or more haptic devices 236 configured to provide the haptic output.

As seen in FIG. 2A, the metaverse controller 220 may comprise a user condition determiner 222 and a presentation controller 224. The metaverse controller 220 may be configured to determine a user condition based on biometrics of a user sensed by one or more biometric sensors 212. The presentation controller 224 may be configured to control one or more metaverse outputs of a metaverse presentation based on the user condition. As indicated, the metaverse outputs may comprise any one or more of a visual output, an audio output, and a haptic output. Recall that in an aspect, the metaverse presentation may comprise a presentation that incorporates extended reality (XR). That is, the metaverse presentation may comprise a presentation that incorporates any combination of VR, AR, MR, gaming, social networking, and so on.

The user condition determiner 222 and the presentation controller 224 may be implemented as separate physical modules. In another aspect, the two may be integrated in a single device or an integrated circuit such as a system-on-chip (SoC). Alternatively, the user condition determiner 222 and the presentation controller 224 may be viewed as logical units and implemented in hardware (e.g., in field programmable gate array (FPGA) or in a combination of hardware and software.

FIG. 2B illustrates an alternative perspective of a metaverse controller 220 that comprises one or more processors 223 and one or more memories 225 communicatively coupled to each other. The memories 225 (e.g., volatile, non-volatile) may be embedded with or separate from the processors 223. The user conditioner 222 and/or the presentation controller 224 may be implemented as computer executable instructions stored in the memories 225 and executed by the processors 223.

Figure 3:
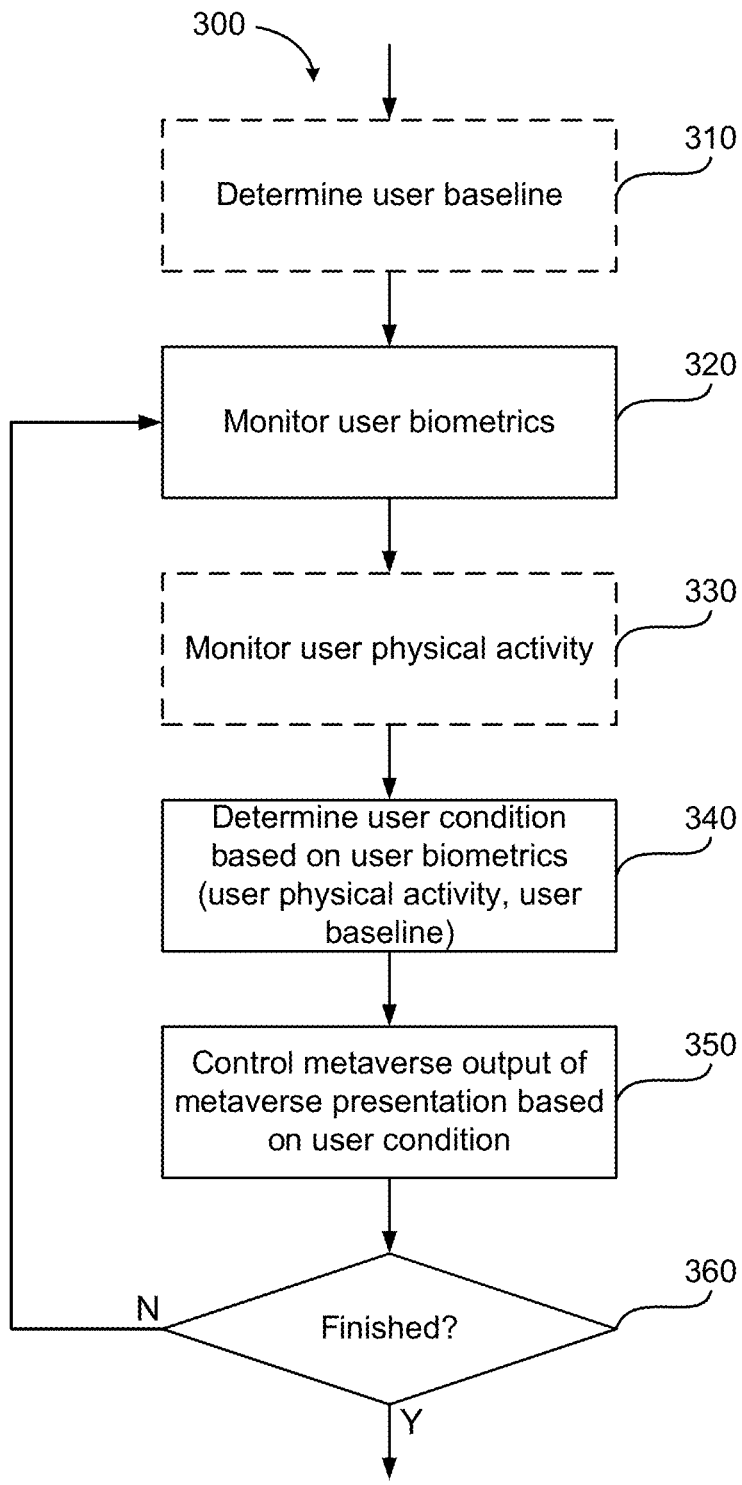
FIGS. 3-7 illustrate flow charts of an example method of controlling a metaverse presentation in accordance with one or more aspects of the disclosure.

FIG. 3 illustrates a flow chart of an example method 300 performed by the metaverse controller 220 for controlling a metaverse presentation to a user. In block 310, the user conditioner determiner 222 may determine or otherwise establish a user baseline.

Figure 4:
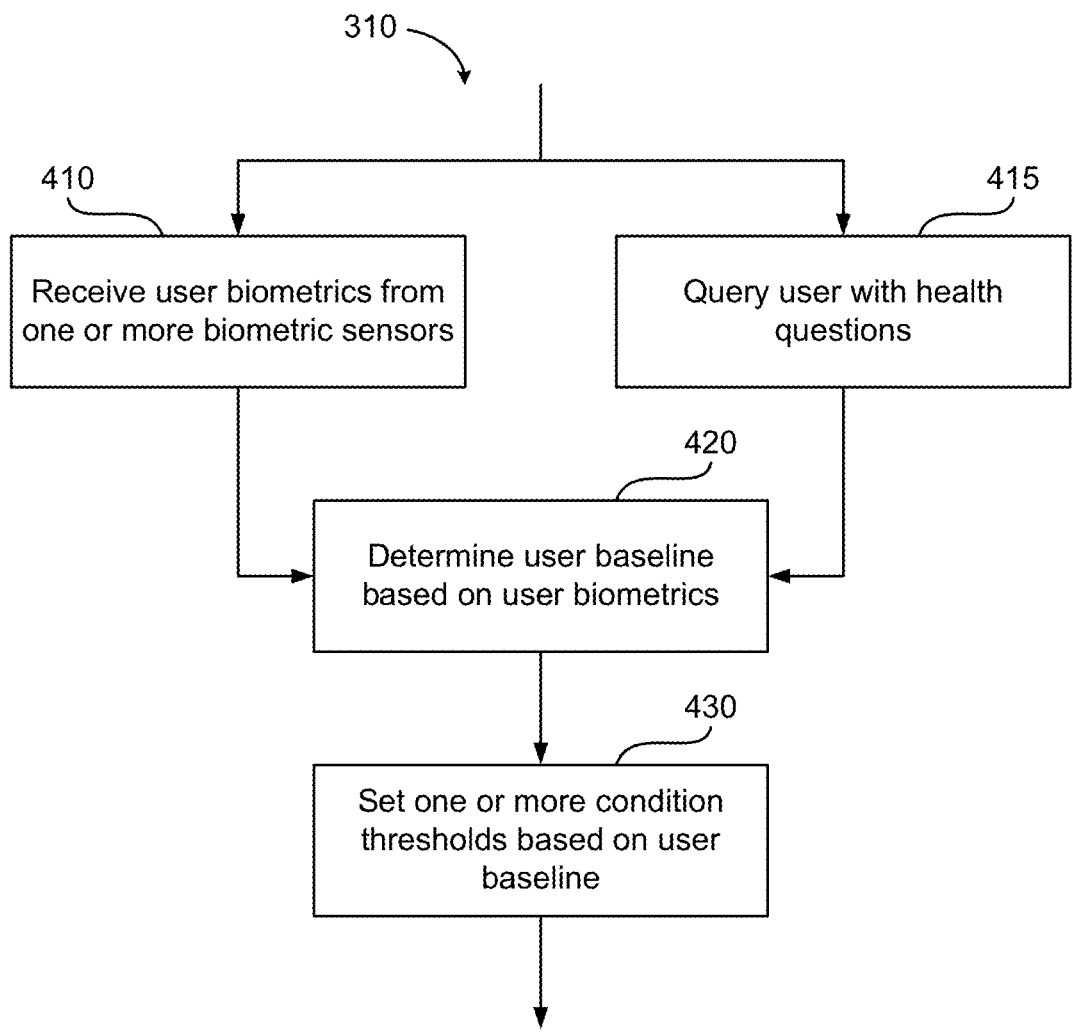

FIG. 4 illustrates a flow chart of a process performed by the user condition determiner 222 (or the processor 223 and the memory 225) to implement block 310. In one aspect, the user baseline may be determined based on the biometrics of the user. In block 410, the user condition determiner 222 may receive user biometrics sensed by the one or more biometric sensors 224. Alternatively or in addition thereto, in block 415, the user condition determiner 222 may query the user with health related questions provided by the user. For example, the user may be asked provide age, sex, weight, height, etc.

In block 420, the user condition determiner 222 may determine the user baseline, which may be based on the user biometrics sensed by the sensors 212, user answers to health questions, or both. For example, baselines in any combination of SPO2, heart rate, body temperature, ECG, blood pressure, etc. may be established.

In block 430, the user condition determiner 222 may set one or more condition thresholds based on the user baseline. In general, the condition thresholds may be utilized to determine a level of user's indulgence in the metaverse presentation. The condition thresholds are described in detail further below.

Referring back to FIG. 3, note that block 310 is dashed to indicate that block 310 is optional. In an aspect, if the user is a new user—i.e., unknown to the system—then block 310 may be performed. If the user is a known user whose baseline has been established previously, then block 310 need not be performed, unless the user wishes to do so again. In another aspect, an unknown user may be unwilling to undergo the baseline determination. In such circumstance, instead of performing block 310, the user condition determiner 222 may simply assume a generic user baseline and generic condition thresholds.

Note that if block 310 is performed, it may be performed at the beginning. In other words, block 310 may be performed before the metaverse presentation being started.

Figure 5:
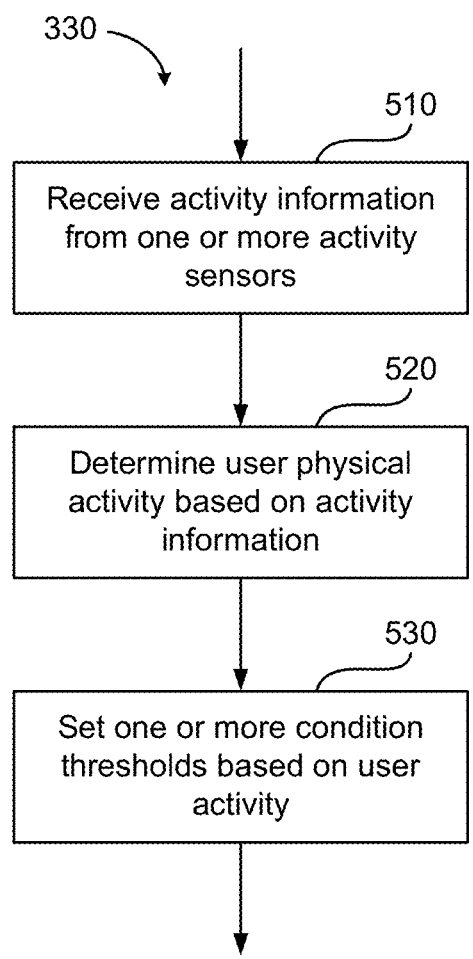

In block 320, the user condition determiner 222 may monitor the user biometrics based on the biometrics sensed by the one or more biometric sensors 212. Again, biometrics such as SP02, heart rate, body temperature, ECG, blood pressure, etc. may be monitored. In block 330, the user condition determiner 222 may monitor the user physical activity. FIG. 5 illustrates a flow chart of a process performed by the user condition determiner 222 (or the processor 223 and the memory 225) to implement block 330. In block 510, the user condition determiner 222 may receive activity information from the one or more activity sensors 214. In an aspect, activity sensors 214 may be configured to provide user motion information. For example, the activity sensors may provide motion information of the user's hands, elbows, knees, feet, head, etc.

In block 520, the user condition determiner 222 may determine the user physical activity based on the activity information. For example, the user may be determined to be sitting, standing, walking, fast walking, running, sprinting, etc. Generally, the user physical activity may one of a plurality of physical activity types, and each physical activity type may be associated with a particular physical exertion level. In an aspect, a corresponding body temperature margin may be assigned. The body temperature margin may be utilized when determining user conditions (described further below). Table 1 below is an example of a table that correlates physical activity types with levels of exertion and temperature margins.

TABLE 1

|  | Standing | Walking | Fast walking | Running | Sprinting |
|---|---|---|---|---|---|
| Intensity | 20% | 40% | 60% | 80% | 100% |
| Body temperature margin | 0 | 0.25 | 0.5 | 0.75 | 1 |

In block 530, the user condition determiner 222 may set the one or more condition thresholds based on the user activity.

Referring back to FIG. 3, in block 340, the user condition determiner 222 may determine the user condition based on the biometrics of the user (e.g., sensed by the one or more biometric sensors 212. The user condition may also be set based on the user baseline, the user activity, or both. In particular, the one or more condition thresholds may be set based on the user baseline (see FIG. 4), the user activity (see FIG. 5), or both.

Figure 6:
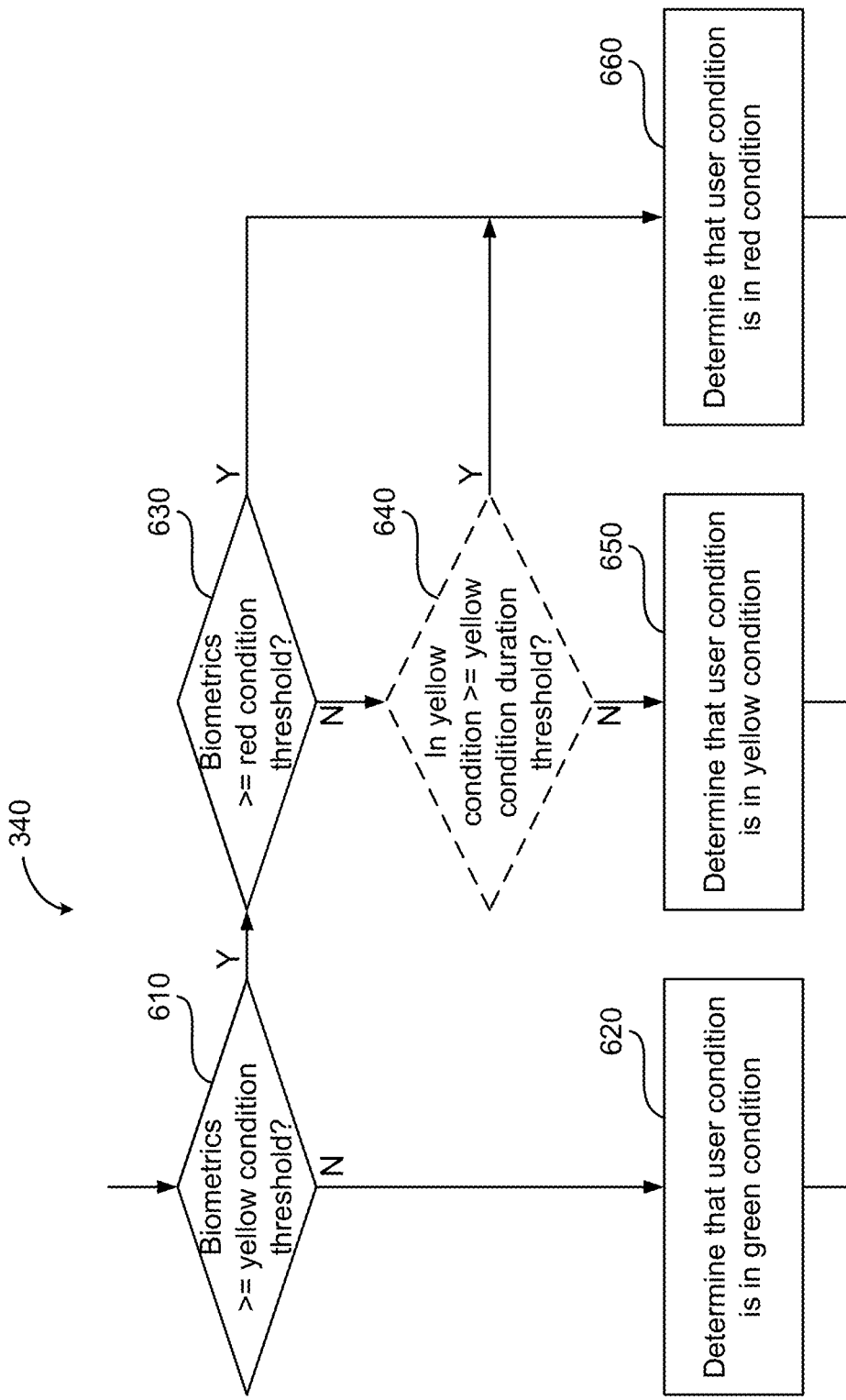

FIG. 6 illustrates a flow chart of a process performed by the user condition determiner 222 (or the processor 223 and the memory 225) to implement block 340. In block 610, the user condition determiner 222 may determine whether the user's biometrics are at or above the yellow condition threshold. For explanation, an example user condition table is provided in Table 2 below.

TABLE 2

|  | Green | Yellow | Red |
|---|---|---|---|
| SPO2 | 95% or more | Under 95% | Under 92% |
| Heart rate | Under target rate: by age, user baseline, exercise intensity | Over target rate: by age, user baseline, exercise intensity | Over 220-age |
| Body temperature | Under 37° C.: by user baseline, body temperature margin | Over 37° C: by user baseline, body temperature margin Under 36° C. (mild hypothermia) | Over 38° C.: by user baseline, body temperature margin Under 35° C. (hypothermia) |
| ECG | Regular pulse |  | Irregular pulse |
| High blood pressure | Under base value of BP table + 10 mmHg | Over base value of BP table + 10 mmHg | Over base value of BP table + 20 mmHg |
| Low blood pressure | Over base value of BP table + 10 mmHg | Under base value of BP table + 10 mmHg | Under base value of BP table + 20 mmHg |

In Table 2, three user conditions are defined—green (or normal), yellow (or cautionary), and red (or critical). This is merely an example. There can be any number of user conditions that may be defined. However, for simplicity of explanation, three conditions are illustrated in table 2. The dividing line between green and yellow conditions may be referred to as the yellow condition threshold.

Note that Table 2 takes into account both user activity and the user baseline in setting the user conditions. For example, regarding heart rate, the green and yellow conditions both account for user's baseline and user activity. For example, a user's target and maximum heart rates may be calculated based on age and exercise intensity as follows:

Maximum heart rate: HRmax=220−age;
Resting heart rate: HRR=heart rate when user is at rest;
Exercise intensity: EI=based on user activity (in %);
Target heart rate: HRT=EI×HRmax+(1−EI)×HRR.

For example, if a 50 year-old user with normal heart rate is exercising at 60% intensity (e.g, fast walking), the target heart rate is 142 (=60%×(220−50)+40%×100). In this instance, in as far as the heart rate is concerned, the user may be considered to be in yellow condition if the heart rate is at or above 142 and in green condition if it is below 142. Also, regardless of age, if the heart rate is at or above the max heart rate HRmax, the user condition may be considered to be in the red condition.

As another example, user body temperature may be used for determining the user condition. As an illustration, user's baseline body temperature may be 36.5° C. If the user physical activity shows an intensity level of 40% (e.g., walking), the user condition may be in green condition up to 36.75° C. (=37+(36−36.5)+0.25). Above that, the user condition may be in yellow condition. The user condition may be in red condition if the body temperature goes above 37.75° C. (=38+(36−36.5)+0.25).

Note that in an aspect, the body temperature may be monitored for hypothermic conditions as well. For example, a body temperature below 36° C. may indicate mild hypothermia and below 35° C. may indicate severe hypothermia.

As a further example, blood pressure may also be utilized. Table 3 illustrates an example of a blood pressure (BP) table that can be used to determine the base values.

TABLE 3

| Age | Male | | | | Female | | | |
| --- | --- | --- | --- | --- | --- | --- | --- | --- |
| | Min diastolic | Max diastolic | Min systolic | Max systolic | Min diastolic | Max diastolic | Min systolic | Max systolic |
| 10~ | 59 | 79 | 110 | 134 | 57 | 75 | 101 | 123 |
| 20~ | 64 | 84 | 113 | 137 | 60 | 78 | 103 | 125 |
| 30~ | 67 | 89 | 114 | 142 | 63 | 83 | 106 | 134 |
| 40~ | 71 | 95 | 126 | 150 | 68 | 90 | 112 | 146 |
| 50~ | 73 | 97 | 121 | 159 | 70 | 94 | 117 | 159 |
| 60~ | 73 | 95 | 124 | 166 | 71 | 93 | 124 | 166 |
| 70~ | 71 | 95 | 128 | 170 | 68 | 94 | 131 | 173 |

In an aspect, if at least some minimum number (e.g., one, two, three, etc.) of biometrics are at or above the yellow condition threshold, the user condition may be determined to be in a yellow condition. For example, if the minimum number is one, then all of the biometrics should be below the yellow condition threshold for the user condition to be in the green condition. In this situation, if any one of the biometrics is at or above the yellow condition threshold, the user condition may be determined to be in the yellow condition. For example, if the user's heart rate is at or above the target rate, the user condition may be determined as being in the yellow condition. If the user's heart rate is below the target rate, the user condition may be determined as being in the yellow condition. Alternatively, if the user's body temperature is at or over 37° C. modified by the baseline and temperature margin, the user condition may be determined to be in the yellow condition. If the user's body temperature is below that level, the user condition may be determined to be in the green condition. Similarly, if any single biometric is at or above the red condition threshold (between yellow and red conditions), then the user condition may be determined to be red condition.

If the user's biometrics are determined to be below the yellow condition threshold ('N' output from block 610), the user condition determiner 222 in block 620 may determine that the user condition is in the green condition.

On the other hand, if the user's biometrics are determined to be at or above the yellow condition threshold ('Y' output from block 610), then in block 630, the user condition determiner 222 may determine whether the user biometrics are at or above the red condition threshold.

If it is determined that the user's biometrics are at or above the red condition threshold ('Y' output from block 630), then in block 660, the user condition determiner 222 may determine that the user condition is in the red condition.

On the other hand, if the user's biometrics are determined to be below the red condition threshold ('N' output from block 630), then in block 650, the user condition determiner 222 (or the processor 223 and the memory 225) may determine that the user condition is in the yellow condition.

In an aspect, it may be undesirable for the user to be in the cautionary state for a long time. For example, it may be undesirable for the user's heart rate to be in an elevated state for too long. Thus, in an alternative, if the user's biometrics are determined to be below the red condition threshold ('N' output from block 630), then in block 640 (dashed to indicate block 640 is optional), the user condition determiner 222 (or the processor 223 and the memory 225) may determine whether the user condition has been in the yellow condition for a duration longer than or equal to red condition threshold duration.

If so ('Y' output from block 640), the user condition determiner 222 (or the processor 223 and the memory 225) may determine that the user condition is in the red condition in block 660. Otherwise ('Y' output from block 640), the user condition determiner 222 (or the processor 223 and the memory 225) may determine that the user condition is in the yellow condition in block 650.

Referring back to FIG. 3, in block 350, the presentation controller 224 may control one or more metaverse outputs of a metaverse presentation based on the user condition. In other words, the presentation controller 224 may control the visual output, the audio output, and/or the haptic output.

Figure 7:
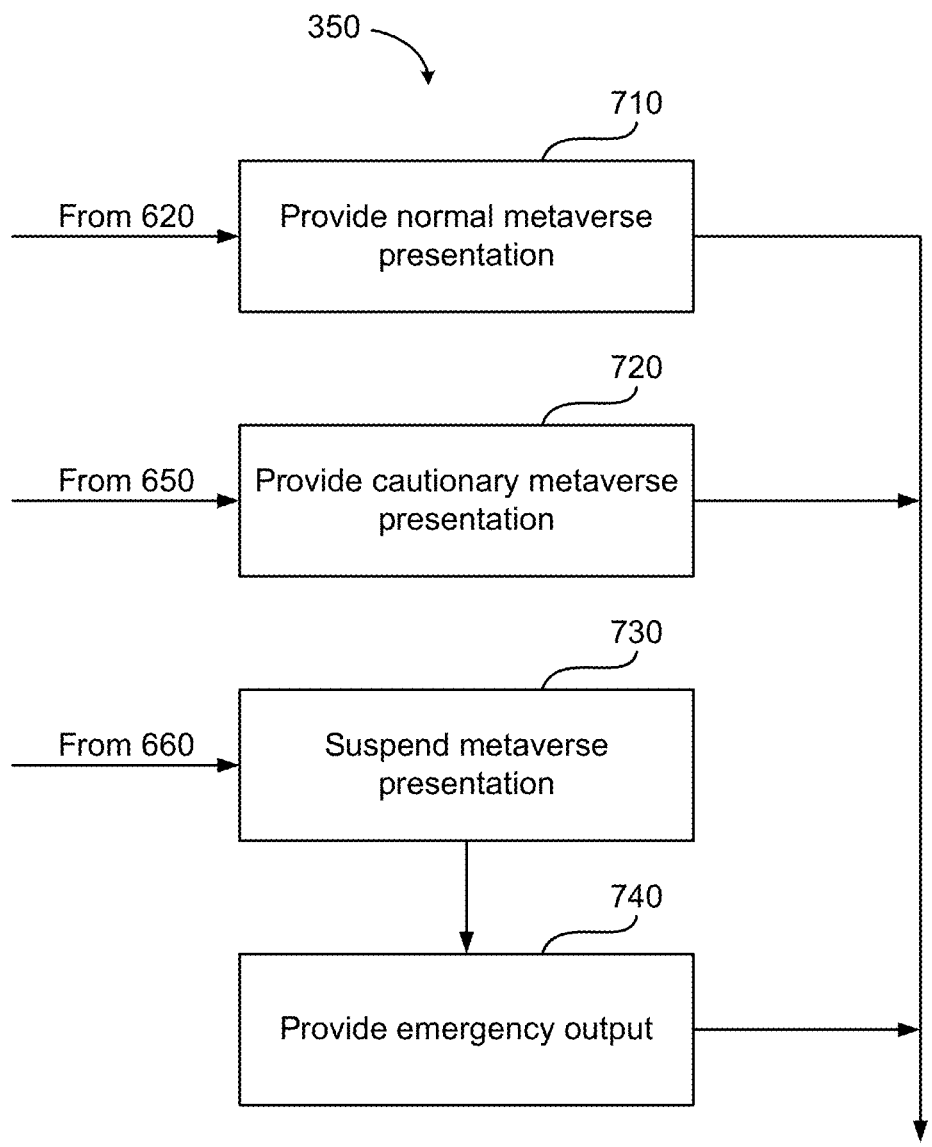

FIG. 7 illustrates a flow chart of a process performed by the presentation controller 224 (or the processor 223 and the memory 225) to implement block 350. If the user condition is determined to be in the green condition (e.g., from block 620), then in block 710, the presentation controller 224 may provide a normal metaverse presentation. In an aspect, the normal metaverse presentation may be the presentation as intended by one or more applications generating the metaverse presentation.

If the user condition is determined to be in the yellow condition (e.g., from block 650), then in block 720, the presentation controller 224 may provide a cautionary metaverse presentation. At the very least, there may be some difference between the normal and cautionary metaverse presentations.

Recall that the metaverse presentation is connected to reality in various ways. In an aspect, the realistic components may be increased in the cautionary metaverse presentation relative to the normal metaverse presentation. Alternatively on in addition thereto, non-realistic components may be decreased in the cautionary metaverse relative to the normal metaverse presentation.

Some of the specific differences between the normal and the cautionary metaverse presentations may include any combination of the following:
brightness of the visual output may be different (e.g., cautionary metaverse presentation may be brighter or darker depending on whichever will disrupt the user engagement);

color saturation of the visual output may be different (e.g., cautionary metaverse presentation may be more or less saturated depending on whichever will disrupt the user engagement);

gray scale of the visual output may be different (e.g., cautionary metaverse presentation may have more or less gray scale depending on whichever will disrupt the user engagement);

visual white noise of the visual output may be different (e.g., cautionary metaverse presentation may have more or less white noise depending on whichever will disrupt the user engagement);

audio white noise of the audio output may be different (e.g., cautionary metaverse presentation may sound more or less white noise depending on whichever will disrupt the user engagement);

vibration of the haptic output may be different (e.g., cautionary metaverse presentation may have stronger or weaker vibration depending on whichever will disrupt the user engagement, cautionary metaverse presentation may have longer or shorter vibration depending on whichever will disrupt the user engagement, cautionary metaverse may have vibration output when the normal metaverse does not, cautionary metaverse may not have vibration output when the normal metaverse does);

warnings may be provided in the cautionary metaverse presentation (e.g., visual warning such as pop-up windows and/or scrolling messages, an audio warning, a haptic warning, etc.).

As discussed above, it may be undesirable for the user to be in the yellow condition for a long period of time. While not shown, the presentation controller 224 may be configured to increase the differentiation between the cautionary metaverse presentation and the normal metaverse presentation longer the user condition remains in the yellow condition. For example, the differences in any one or more of brightness, color saturation, gray scale, visual white noise, audio white noise, haptic output vibration, warnings, etc. may be increased.

If the user condition is determined to be in the red condition (e.g., from block 660), then in block 730, the presentation controller 224 may suspend the metaverse presentation altogether.

In block 740, the presentation controller 224 may also provide emergency outputs. For example, the presentation controller 224 may control the metaverse outputs in any combination of the following ways:

output a single color on the visual output;
output an audible alert on the audio output;
output a vibration lasting longer than a critical duration on the haptic output;
output an alert window on the visual output;
notify an emergency contact (e.g., call 911, call a designated emergency contact, etc.)

Referring back to FIG. 3, the metaverse controller 220 (or the processor 223 and the memory 225) in block 360 may check whether the metaverse presentation has finished. If not ('N' output from block 360, then method may proceed to block 320. If so ('Y' output from block 360, then method may finish.

It is thus seen that the user biometrics may be monitored multiple times. In an aspect, a frequency of performing block 320 may be set based on the user condition. For example, if the user condition is in the green condition, the user condition determiner 222 may wait a first time duration before performing block 320 again. If the user condition is in the yellow condition, the user condition determiner 222 may wait a second time duration before performing block 320 again. The second time duration may be [shorted] shorter than the first time duration. That is, the user condition determiner 222 may monitor the user biometrics more frequently while that user is in the yellow condition than while the user is in the green condition.

Figure 8:
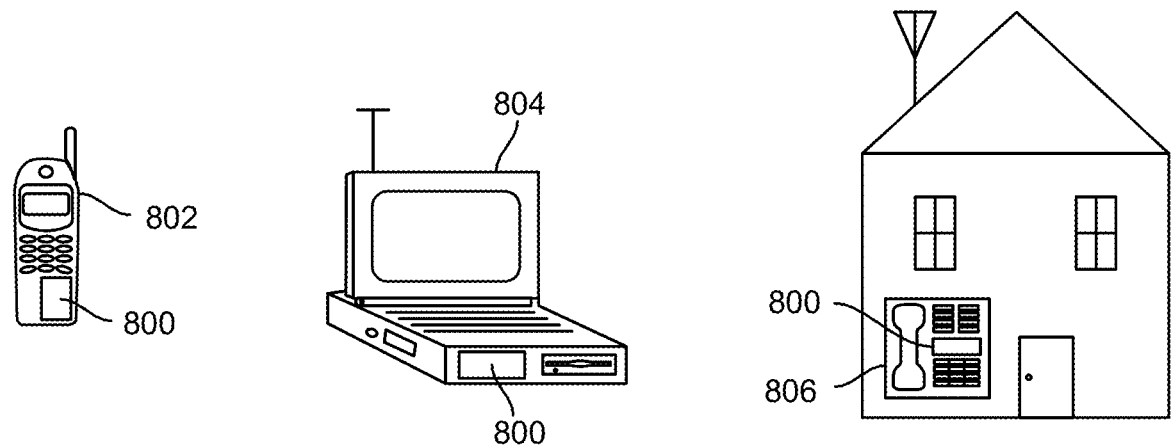
FIG. 8 illustrates various electronic devices which may utilize one or more aspects of the disclosure.

FIG. 8 illustrates various electronic devices 800 that may be integrated with any of the aforementioned metaverse controller in accordance with various aspects of the disclosure. For example, a mobile phone device 802, a laptop computer device 804, and a fixed location terminal device 806 may each be considered generally user equipment (UE) and may include the metaverse controller as described herein. The devices 802, 804, 806 illustrated in FIG. 8 are merely exemplary. Other electronic devices may also include the RF filter including, but not limited to, a group of devices (e.g., electronic devices) that includes mobile devices, hand-held personal communication systems (PCS) units, portable data units such as personal digital assistants, global positioning system (GPS) enabled devices, navigation devices, set top boxes, music players, video players, entertainment units, fixed location data units such as meter reading equipment, communications devices, smartphones, tablet computers, computers, wearable devices, servers, routers, electronic devices implemented in automotive vehicles (e.g., autonomous vehicles), an Internet of things (IoT) device or any other device that stores or retrieves data or computer instructions or any combination thereof.

Implementation examples are described in the following numbered clauses:

Clause 1: A metaverse controller comprising: a user condition determiner configured to determine a user condition based on biometrics of a user sensed by one or more biometric sensors; and a presentation controller configured to control one or more metaverse outputs of a metaverse presentation based on the user condition, the metaverse outputs comprising any one or more of a visual output, an audio output, and a haptic output, and the metaverse presentation comprising a presentation that incorporates extended reality (XR).

Clause 2: The metaverse controller of clause 1, wherein the XR comprises any one or more of a virtual reality (VR), an augmented reality (AR), a mixed reality (MR), gaming, and social networking.

Clause 3: The metaverse controller of any of clauses 1-2, wherein the biometrics sensed by the one or biometric sensors comprise any one or more of oxygen saturation (SPO2), heart rate, body temperature, and blood pressure.

Clause 4: The metaverse controller of any of clauses 1-3, wherein the one or more biometric sensors comprise a superficial temporal artery sensor.

Clause 5: The metaverse controller of clause 4, wherein the superficial temporal artery sensor is mounted on or is integrated with a head mounted display (HMD), the HMD being configured to display the visual output.

Clause 6: The metaverse controller of any of clauses 1-5, wherein the user condition determiner is configured to: determine whether the biometrics are at or above a yellow condition threshold; determine that the user condition is in a yellow condition upon determining that the biometrics are at or above the yellow condition threshold; and determine that the user condition is in a green condition upon determining that the biometrics are below the yellow condition threshold, and wherein the presentation controller is configured to control the metaverse outputs to provide a normal metaverse presentation upon the user condition being determined to be in the green condition, and a cautionary metaverse presentation different from the normal metaverse presentation upon the user condition being determined to be in the yellow condition.

Clause 7: The metaverse controller of clause 6, wherein a realistic component presentation is increased in the cautionary metaverse presentation relative to the normal metaverse presentation, wherein a non-realistic component presentation is decreased in the cautionary metaverse presentation relative to the normal metaverse presentation, or both.

Clause 8: The metaverse controller of any of clauses 6-7, wherein the normal metaverse presentation is a presentation as intended by an application generating the metaverse presentation, and wherein the cautionary metaverse presentation is a presentation that deviates from the normal metaverse presentation.

Clause 9: The metaverse controller of any of clauses 6-8, wherein a brightness of the visual output is different between the cautionary metaverse presentation and the normal metaverse presentation, wherein a color saturation of the visual output is different between the cautionary metaverse presentation and the normal metaverse presentation, wherein a gray scale of the visual output is different between the cautionary metaverse presentation and the normal metaverse presentation, wherein a visual white noise of the visual output is different between the cautionary metaverse presentation and the normal metaverse presentation, wherein an audio white noise of the audio output is different between the cautionary metaverse presentation and the normal metaverse presentation, wherein a vibration of the haptic output is different between the cautionary metaverse presentation and the normal metaverse presentation, wherein any one or more of a visual warning, an audio warning, or a haptic warning is presented in the cautionary metaverse presentation, or any combination thereof.

Clause 10: The metaverse controller of any of clauses 6-9, wherein the user condition determiner is configured to determine the user condition again after a first time duration upon determining that the user condition is in the green condition, and after a second time duration upon determining that the user condition is in the yellow condition, the second time duration being shorter than the first time duration.

Clause 11: The metaverse controller of any of clauses 6-10, wherein the presentation controller is configured to increase a differentiation between the cautionary metaverse presentation and the normal metaverse presentation longer the user condition remains in the yellow condition.

Clause 12: The metaverse controller of any of clauses 6-11, wherein the user condition determiner is further configured to: determine whether the biometrics are at or above a red condition threshold, the red condition threshold being higher than the yellow condition threshold; and determine that the user condition is in a red condition upon determining that the biometrics are at or above the red condition threshold, and wherein the presentation controller is further configured to control the metaverse outputs to suspend the metaverse presentation upon the user condition being determined to be in the red condition.

Clause 13: The metaverse controller of clause 12, wherein upon the user condition being determined to be in the red condition, the presentation controller is further configured to control the metaverse outputs to output a single color on the visual output, output an audible alert on the audio output, output a vibration lasting longer than a critical duration on the haptic output, output an alert window on the visual output, notify an emergency contact, or any combination thereof.

Clause 14: The metaverse controller of any of clauses 12-13, wherein the user condition determiner is further configured to: determine whether the user condition has been in the yellow condition longer than or equal to a yellow condition duration threshold; and determine that the user condition is in a red condition upon determining that the user condition has been in the yellow condition longer than or equal to a red condition threshold duration.

Clause 15: The metaverse controller of any of clauses 6-14, wherein user condition determiner is further configured to determine a user physical activity based on activity information received from one or more activity sensors, and set one or more condition thresholds based on the user physical activity, the one or more condition thresholds including the yellow condition threshold.

Clause 16: The metaverse controller of clause 15, wherein the user physical activity is one of a plurality of physical activity types, each physical activity type being associated with a physical exertion level.

Clause 17: The metaverse controller of any of clauses 15-16, wherein the user physical activity determined from a set of physical activity type, the set comprising one or more of sitting, standing, walking, fast walking, jogging, running, and sprinting.

Clause 18: The metaverse controller of any of clauses 6-17, wherein the user condition determiner is further configured to determine a user baseline, and set one or more condition thresholds based on the user baseline, the one or more condition thresholds including the yellow condition threshold.

Clause 19: The metaverse controller of clause 18, wherein the user condition determiner configured to determine the user baseline based on the biometrics of the user sensed by the one or more biometric sensors, user answers to health questions, or both.

Clause 20: The metaverse controller of any of clauses 18-19, wherein the user condition determiner configured to determine the user baseline prior to the metaverse presentation being started.

Clause 21: A method of controlling a metaverse presentation, the method comprising: determining a user condition based on biometrics of a user sensed by one or more biometric sensors; and controlling one or more metaverse outputs of a metaverse presentation based on the user condition, the metaverse outputs comprising any one or more of a visual output, an audio output, and a haptic output, and the metaverse presentation comprising a presentation that incorporates extended reality (XR).

Clause 22: The method of clause 21, wherein the XR comprises any one or more of a virtual reality (VR), an augmented reality (AR), a mixed reality (MR), gaming, and social networking.

Clause 23: The method of any of clauses 21-22, wherein the biometrics sensed by the one or biometric sensors comprise any one or more of oxygen saturation (SPO2), heart rate, body temperature, and blood pressure.

Clause 24: The method of any of clauses 21-23, wherein the one or more biometric sensors comprise a superficial temporal artery sensor.

Clause 25: The method of clause 24, wherein the superficial temporal artery sensor is mounted on or is integrated with a head mounted display (HMD), the HMD being configured to display the visual output.

Clause 26: The method of any of clauses 21-25, wherein determining the user condition comprises: determining whether the biometrics are at or above a yellow condition threshold; determining that the user condition is in a yellow condition upon determining that the biometrics are at or above the yellow condition threshold; and determining that the user condition is in a green condition upon determining that the biometrics are below the yellow condition threshold, and wherein controlling the one or more metaverse outputs comprises: providing a normal metaverse presentation upon the user condition being determined to be in the green condition; and providing a cautionary metaverse presentation different from the normal metaverse presentation upon the user condition being determined to be in the yellow condition.

Clause 27: The method of clause 26, wherein a realistic component presentation is increased in the cautionary metaverse presentation relative to the normal metaverse presentation, wherein a non-realistic component presentation is decreased in the cautionary metaverse presentation relative to the normal metaverse presentation, or both.

Clause 28: The method of any of clauses 26-27, wherein the normal metaverse presentation is a presentation as intended by an application generating the metaverse presentation, and wherein the cautionary metaverse presentation is a presentation that deviates from the normal metaverse presentation.

Clause 29: The method of any of clauses 26-28, wherein a brightness of the visual output is different between the cautionary metaverse presentation and the normal metaverse presentation, wherein a color saturation of the visual output is different between the cautionary metaverse presentation and the normal metaverse presentation, wherein a gray scale of the visual output is different between the cautionary metaverse presentation and the normal metaverse presentation, wherein a visual white noise of the visual output is different between the cautionary metaverse presentation and the normal metaverse presentation, wherein an audio white noise of the audio output is different between the cautionary metaverse presentation and the normal metaverse presentation, wherein a vibration of the haptic output is different between the cautionary metaverse presentation and the normal metaverse presentation, wherein any one or more of a visual warning, an audio warning, or a haptic warning is presented in the cautionary metaverse presentation, or any combination thereof.

Clause 30: The method of any of clauses 26-29, wherein the user condition is determined again after a first time duration upon determining that the user condition is in the green condition, and after a second time duration upon determining that the user condition is in the yellow condition, the second time duration being shorter than the first time duration.

Clause 31: The method of any of clauses 26-30, wherein a differentiation between the cautionary metaverse presentation and the normal metaverse presentation is increased longer the user condition remains in the yellow condition.

Clause 32: The method of any of clauses 26-31, wherein determining the user condition further comprises: determining whether the biometrics are at or above a red condition threshold, the red condition threshold being higher than the yellow condition threshold; and determine that the user condition is in a red condition upon determining that the biometrics are at or above the red condition threshold, and wherein controlling the one or more metaverse outputs further comprises suspending the metaverse presentation upon the user condition being determined to be in the red condition.

Clause 33: The method of clause 32, wherein upon the user condition being determined to be in the red condition, controlling the one or more metaverse outputs comprises: outputting a single color on the visual output, outputting an audible alert on the audio output, outputting a vibration lasting longer than a critical duration on the haptic output, outputting an alert window on the visual output, notifying an emergency contact, or any combination thereof.

Clause 34: The method of any of clauses 32-33, wherein determining the user condition further comprises: determining whether the user condition has been in the yellow condition longer than or equal to a yellow condition duration threshold; and determining that the user condition is in a red condition upon determining that the user condition has been in the yellow condition longer than or equal to a red condition threshold duration.

Clause 35: The method of any of clauses 26-34, wherein determining the user condition further comprises: determining a user physical activity based on activity information received from one or more activity sensors; and setting one or more condition thresholds based on the user physical activity, the one or more condition thresholds including the yellow condition threshold.

Clause 36: The method of clause 35, wherein the user physical activity is one of a plurality of physical activity types, each physical activity type being associated with a physical exertion level.

Clause 37: The method of any of clauses 35-36, wherein the user physical activity determined from a set of physical activity type, the set comprising one or more of sitting, standing, walking, fast walking, jogging, running, and sprinting.

Clause 38: The method of any of clauses 26-37, wherein determining the user condition further comprises: determining a user baseline; and setting one or more condition thresholds based on the user baseline, the one or more condition thresholds including the yellow condition threshold.

Clause 39: The method of clause 38, wherein the user baseline is determined based on the biometrics of the user sensed by the one or more biometric sensors, user answers to health questions, or both.

Clause 40: The method of any of clauses 38-39, wherein the user baseline is determined prior to the metaverse presentation being started.

Clause 41: A metaverse controller comprising at least one means for perfo9rming a method of any of clauses 21-40.

Clause 42: A non-transitory computer-readable medium storing code for a metaverse controller comprising one or more memories and one or more processors communicatively connected to the one or more memories, and instructions stored in the one or more memories and executable by the one or more processors to cause the metaverse controller to perform a method of any of clauses 21-40.

As used herein, the terms "user equipment" (or "UE"), "user device," "user terminal," "client device," "communication device," "wireless device," "wireless communications device," "handheld device," "mobile device," "mobile terminal," "mobile station," "handset," "access terminal," "subscriber device," "subscriber terminal," "subscriber station," "terminal," and variants thereof may interchangeably refer to any suitable mobile or stationary device that can receive wireless communication and/or navigation signals. These terms include, but are not limited to, a music player, a video player, an entertainment unit, a navigation device, a communications device, a smartphone, a personal digital assistant, a fixed location terminal, a tablet computer, a computer, a wearable device, a laptop computer, a server, an automotive device in an automotive vehicle, and/or other types of portable electronic devices typically carried by a person and/or having communication capabilities (e.g., wireless, cellular, infrared, short-range radio, etc.). These terms are also intended to include devices which communicate with another device that can receive wireless communication and/or navigation signals such as by short-range wireless, infrared, wireline connection, or other connection, regardless of whether satellite signal reception, assistance data reception, and/or position-related processing occurs at the device or at the other device. In addition, these terms are intended to include all devices, including wireless and wireline communication devices, that are able to communicate with a core network via a radio access network (RAN), and through the core network the UEs can be connected with external networks such as the Internet and with other UEs. Of course, other mechanisms of connecting to the core network and/or the Internet are also possible for the UEs, such as over a wired access network, a wireless local area network (WLAN) (e.g., based on IEEE 802.11, etc.) and so on. UEs can be embodied by any of a number of types of devices including but not limited to printed circuit (PC) cards, compact flash devices, external or internal modems, wireless or wireline phones, smartphones, tablets, tracking devices, asset tags, and so on. A communication link through which UEs can send signals to a RAN is called an uplink channel (e.g., a reverse traffic channel, a reverse control channel, an access channel, etc.). A communication link through which the RAN can send signals to UEs is called a downlink or forward link channel (e.g., a paging channel, a control channel, a broadcast channel, a forward traffic channel, etc.). As used herein the term traffic channel (TCH) can refer to either an uplink/reverse or downlink/forward traffic channel.

The wireless communication between electronic devices can be based on different technologies, such as code division multiple access (CDMA), W-CDMA, time division multiple access (TDMA), frequency division multiple access (FDMA), Orthogonal Frequency Division Multiplexing (OFDM), Global System for Mobile Communications (GSM), 3GPP Long Term Evolution (LTE), 5G New Radio, Bluetooth (BT), Bluetooth Low Energy (BLE), IEEE 802.11 (WiFi), and IEEE 802.15.4 (Zigbee/Thread) or other protocols that may be used in a wireless communications network or a data communications network. Bluetooth Low Energy (also known as Bluetooth LE, BLE, and Bluetooth Smart) is a wireless personal area network technology designed and marketed by the Bluetooth Special Interest Group intended to provide considerably reduced power consumption and cost while maintaining a similar communication range. BLE was merged into the main Bluetooth standard in 2010 with the adoption of the Bluetooth Core Specification Version 4.0 and updated in Bluetooth 5.

The word "exemplary" is used herein to mean "serving as an example, instance, or illustration." Any details described herein as "exemplary" is not to be construed as advantageous over other examples. Likewise, the term "examples" does not mean that all examples include the discussed feature, advantage or mode of operation. Furthermore, a particular feature and/or structure can be combined with one or more other features and/or structures. Moreover, at least a portion of the apparatus described herein can be configured to perform at least a portion of a method described herein.

It should be noted that the terms "connected," "coupled," or any variant thereof, mean any connection or coupling, either direct or indirect, between elements, and can encompass a presence of an intermediate element between two elements that are "connected" or "coupled" together via the intermediate element unless the connection is expressly disclosed as being directly connected.

Any reference herein to an element using a designation such as "first," "second," and so forth does not limit the quantity and/or order of those elements. Rather, these designations are used as a convenient method of distinguishing between two or more elements and/or instances of an element. Also, unless stated otherwise, a set of elements can comprise one or more elements.

Those skilled in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Nothing stated or illustrated depicted in this application is intended to dedicate any component, action, feature, benefit, advantage, or equivalent to the public, regardless of whether the component, action, feature, benefit, advantage, or the equivalent is recited in the claims.

In the detailed description above it can be seen that different features are grouped together in examples. This manner of disclosure should not be understood as an intention that the claimed examples have more features than are explicitly mentioned in the respective claim. Rather, the disclosure may include fewer than all features of an individual example disclosed. Therefore, the following claims should hereby be deemed to be incorporated in the description, wherein each claim by itself can stand as a separate example. Although each claim by itself can stand as a separate example, it should be noted that—although a dependent claim can refer in the claims to a specific combination with one or one or more claims—other examples can also encompass or include a combination of said dependent claim with the subject matter of any other dependent claim or a combination of any feature with other dependent and independent claims. Such combinations are proposed herein, unless it is explicitly expressed that a specific combination is not intended. Furthermore, it is also intended that features of a claim can be included in any other independent claim, even if said claim is not directly dependent on the independent claim.

It should furthermore be noted that methods, systems, and apparatus disclosed in the description or in the claims can be implemented by a device comprising means for performing the respective actions and/or functionalities of the methods disclosed.

Furthermore, in some examples, an individual action can be subdivided into one or more sub-actions or contain one or more sub-actions. Such sub-actions can be contained in the disclosure of the individual action and be part of the disclosure of the individual action.

While the foregoing disclosure shows illustrative examples of the disclosure, it should be noted that various changes and modifications could be made herein without departing from the scope of the disclosure as defined by the appended claims. The functions and/or actions of the method claims in accordance with the examples of the disclosure described herein need not be performed in any particular order. Additionally, well-known elements will not be described in detail or may be omitted so as to not obscure the relevant details of the aspects and examples disclosed herein. Furthermore, although elements of the disclosure may be described or claimed in the singular, the plural is contemplated unless limitation to the singular is explicitly stated.

What is claimed is:

1. A metaverse controller comprising:
a user condition determiner configured to determine a user condition based on biometrics of a user sensed by one or more biometric sensors; and
a presentation controller configured to control one or more metaverse outputs of a metaverse presentation based on the user condition, the metaverse presentation being presented to the user, the metaverse outputs comprising any one or more of a visual output, an audio output, and a haptic output, and the metaverse presentation comprising a presentation that incorporates extended reality (XR),
wherein the user condition determiner is configured to:
determine whether the biometrics are at or above a yellow condition threshold;
determine that the user condition is in a yellow condition upon determining that the biometrics are at or above the yellow condition threshold; and
determine that the user condition is in a green condition upon determining that the biometrics are below the yellow condition threshold,
wherein the presentation controller is configured to control the metaverse outputs to provide a normal metaverse presentation upon the user condition being determined to be in the green condition, and a cautionary metaverse presentation different from the normal metaverse presentation upon the user condition being determined to be in the yellow condition, and
wherein an amount of differentiation between the cautionary metaverse presentation and the normal metaverse presentation corresponds to a duration the user condition remains in the yellow condition.

2. The metaverse controller of claim 1, wherein the XR comprises any one or more of a virtual reality (VR), an augmented reality (AR), a mixed reality (MR), gaming, and social networking.

3. The metaverse controller of claim 1, wherein the biometrics sensed by the one or biometric sensors comprise any one or more of oxygen saturation (SPO2), heart rate, body temperature, and blood pressure.

4. The metaverse controller of claim 1, wherein the one or more biometric sensors comprise a superficial temporal artery sensor.

5. The metaverse controller of claim 4, wherein the superficial temporal artery sensor is mounted on or is integrated with a head mounted display (HMD), the HMD being configured to display the visual output.

6. The metaverse controller of claim 1,
wherein a realistic component presentation is increased in the cautionary metaverse presentation relative to the normal metaverse presentation,
wherein a non-realistic component presentation is decreased in the cautionary metaverse presentation relative to the normal metaverse presentation, or both.

7. The metaverse controller of claim 1,
wherein the normal metaverse presentation is a presentation as intended by an application generating the metaverse presentation, and
wherein the cautionary metaverse presentation is a presentation that deviates from the normal metaverse presentation.

8. The metaverse controller of claim 1,
wherein a brightness of the visual output is different between the cautionary metaverse presentation and the normal metaverse presentation,
wherein a color saturation of the visual output is different between the cautionary metaverse presentation and the normal metaverse presentation,
wherein a gray scale of the visual output is different between the cautionary metaverse presentation and the normal metaverse presentation,
wherein a visual white noise of the visual output is different between the cautionary metaverse presentation and the normal metaverse presentation,
wherein an audio white noise of the audio output is different between the cautionary metaverse presentation and the normal metaverse presentation,
wherein a vibration of the haptic output is different between the cautionary metaverse presentation and the normal metaverse presentation,
wherein any one or more of a visual warning, an audio warning, or a haptic warning is presented in the cautionary metaverse presentation, or
any combination thereof.

9. The metaverse controller of claim 1, wherein the user condition determiner is configured to determine the user condition again after a first time duration upon determining that the user condition is in the green condition, and after a second time duration upon determining that the user condition is in the yellow condition, the second time duration being shorter than the first time duration.

10. The metaverse controller of claim 1, wherein the presentation controller is configured to increase a differentiation between the cautionary metaverse presentation and the normal metaverse presentation longer the user condition remains in the yellow condition.

11. The metaverse controller of claim 1,
wherein the user condition determiner is further configured to:
determine whether the biometrics are at or above a red condition threshold, the red condition threshold being higher than the yellow condition threshold; and
determine that the user condition is in a red condition upon determining that the biometrics are at or above the red condition threshold, and
wherein the presentation controller is further configured to control the metaverse outputs to suspend the metaverse presentation upon the user condition being determined to be in the red condition.

12. The metaverse controller of claim 11, wherein upon the user condition being determined to be in the red condition, the presentation controller is further configured to
control the metaverse outputs to
output a single color on the visual output,
output an audible alert on the audio output,
output a vibration lasting longer than a critical duration on the haptic output,
output an alert window on the visual output,
notify an emergency contact, or
any combination thereof.

13. The metaverse controller of claim 11, wherein the user condition determiner is further configured to:

determine whether the user condition has been in the yellow condition longer than or equal to a yellow condition duration threshold; and determine that the user condition is in a red condition upon determining that the user condition has been in the yellow condition longer than or equal to a red condition threshold duration.

14. The metaverse controller of claim 1, wherein user condition determiner is further configured to determine a user physical activity based on activity information received from one or more activity sensors, and set one or more condition thresholds based on the user physical activity, the one or more condition thresholds including the yellow condition threshold.

15. The metaverse controller of claim 14, wherein the user physical activity is one of a plurality of physical activity types, each physical activity type being associated with a physical exertion level.

16. The metaverse controller of claim 14, wherein the user physical activity determined from a set of physical activity type, the set comprising one or more of sitting, standing, walking, fast walking, jogging, running, and sprinting.

17. The metaverse controller of claim 1, wherein the user condition determiner is further configured to determine a user baseline, and set one or more condition thresholds based on the user baseline, the one or more condition thresholds including the yellow condition threshold.

18. The metaverse controller of claim 17, wherein the user condition determiner configured to determine the user baseline based on the biometrics of the user sensed by the one or more biometric sensors, user answers to health questions, or both.

19. The metaverse controller of claim 17, wherein the user condition determiner configured to determine the user baseline prior to the metaverse presentation being started.

20. A method of controlling a metaverse presentation, the method comprising:

determining a user condition based on biometrics of a user sensed by one or more biometric sensors; and controlling one or more metaverse outputs of a metaverse presentation based on the user condition, the metaverse presentation being presented to the user, the metaverse outputs comprising any one or more of a visual output, an audio output, and a haptic output, and the metaverse presentation comprising a presentation that incorporates extended reality (XR), wherein determining the user condition comprises:

determining whether the biometrics are at or above a yellow condition threshold;

determining that the user condition is in a yellow condition upon determining that the biometrics are at or above the yellow condition threshold; and determining that the user condition is in a green condition upon determining that the biometrics are below the yellow condition threshold, wherein controlling the one or more metaverse outputs comprises:

providing a normal metaverse presentation upon the user condition being determined to be in the green condition; and providing a cautionary metaverse presentation different from the normal metaverse presentation upon the user condition being determined to be in the yellow condition, and wherein an amount of differentiation between the cautionary metaverse presentation and the normal metaverse presentation corresponds to a duration the user condition remains in the yellow condition.

21. The method of claim 20, wherein the XR comprises any one or more of a virtual reality (VR), an augmented reality (AR), a mixed reality (MR), gaming, and social networking.

22. The method of claim 20, wherein the biometrics sensed by the one or biometric sensors comprise any one or more of oxygen saturation (SPO2), heart rate, body temperature, and blood pressure.

23. The method of claim 20, wherein the one or more biometric sensors comprise a superficial temporal artery sensor.

24. The method of claim 23, wherein the superficial temporal artery sensor is mounted on or is integrated with a head mounted display (HMD), the HMD being configured to display the visual output.

25. The method of claim 20, wherein a realistic component presentation is increased in the cautionary metaverse presentation relative to the normal metaverse presentation, wherein a non-realistic component presentation is decreased in the cautionary metaverse presentation relative to the normal metaverse presentation, or both.

26. The method of claim 20, wherein the normal metaverse presentation is a presentation as intended by an application generating the metaverse presentation, and wherein the cautionary metaverse presentation is a presentation that deviates from the normal metaverse presentation.

27. The method of claim 20, wherein a brightness of the visual output is different between the cautionary metaverse presentation and the normal metaverse presentation, wherein a color saturation of the visual output is different between the cautionary metaverse presentation and the normal metaverse presentation, wherein a gray scale of the visual output is different between the cautionary metaverse presentation and the normal metaverse presentation, wherein a visual white noise of the visual output is different between the cautionary metaverse presentation and the normal metaverse presentation, wherein an audio white noise of the audio output is different between the cautionary metaverse presentation and the normal metaverse presentation, wherein a vibration of the haptic output is different between the cautionary metaverse presentation and the normal metaverse presentation, wherein any one or more of a visual warning, an audio warning, or a haptic warning is presented in the cautionary metaverse presentation, or any combination thereof.

28. The method of claim 20, wherein the user condition is determined again after a first time duration upon determining that the user condition is in the green condition, and after a second time duration upon determining that the user condition is in the yellow condition, the second time duration being shorter than the first time duration.

29. The method of claim 20, wherein a differentiation between the cautionary metaverse presentation and the normal metaverse presentation is increased longer the user condition remains in the yellow condition.

30. The method of claim 20,
wherein determining the user condition further comprises:
determining whether the biometrics are at or above a red condition threshold, the red condition threshold being higher than the yellow condition threshold; and
determine that the user condition is in a red condition upon determining that the biometrics are at or above the red condition threshold, and
wherein controlling the one or more metaverse outputs further comprises suspending (730) the metaverse presentation upon the user condition being determined to be in the red condition.

31. The method of claim 30, wherein upon the user condition being determined to be in the red condition, controlling the one or more metaverse outputs comprises:
outputting a single color on the visual output,
outputting an audible alert on the audio output,
outputting a vibration lasting longer than a critical duration on the haptic output,
outputting an alert window on the visual output,
notifying an emergency contact, or
any combination thereof.

32. The method of claim 30, wherein determining the user condition further comprises:
determining whether the user condition has been in the yellow condition longer than or equal to a yellow condition duration threshold; and
determining that the user condition is in a red condition upon determining that the user condition has been in the yellow condition longer than or equal to a red condition threshold duration.

33. The method of claim 20, wherein determining the user condition further comprises:
determining a user physical activity based on activity information received from one or more activity sensors; and
setting one or more condition thresholds based on the user physical activity, the one or more condition thresholds including the yellow condition threshold.

34. The method of claim 33, wherein the user physical activity is one of a plurality of physical activity types, each physical activity type being associated with a physical exertion level.

35. The method of claim 33, wherein the user physical activity determined from a set of physical activity type, the set comprising one or more of sitting, standing, walking, fast walking, jogging, running, and sprinting.

36. The method of claim 20, wherein determining the user condition further comprises:
determining a user baseline; and
setting one or more condition thresholds based on the user baseline, the one or more condition thresholds including the yellow condition threshold.

37. The method of claim 36, wherein the user baseline is determined based on the biometrics of the user sensed by the one or more biometric sensors, user answers to health questions, or both.

38. The method of claim 36, wherein the user baseline is determined prior to the metaverse presentation being started.

39. A metaverse controller comprising:
means for determining a user condition based on biometrics of a user sensed by one or more biometric sensors; and
means for controlling one or more metaverse outputs of a metaverse presentation based on the user condition, the metaverse presentation being presented to the user, the metaverse outputs comprising any one or more of a visual output, an audio output, and a haptic output, and the metaverse presentation comprising a presentation that incorporates extended reality (XR),
wherein the means for determining:
determine whether the biometrics are at or above a yellow condition threshold;
determine that the user condition is in a yellow condition upon determining that the biometrics are at or above the yellow condition threshold; and
determine that the user condition is in a green condition upon determining that the biometrics are below the yellow condition threshold,
wherein the means for controlling control the metaverse outputs to provide a normal metaverse presentation upon the user condition being determined to be in the green condition, and a cautionary metaverse presentation different from the normal metaverse presentation upon the user condition being determined to be in the yellow condition, and
wherein an amount of differentiation between the cautionary metaverse presentation and the normal metaverse presentation corresponds to a duration the user condition remains in the yellow condition.

40. A non-transitory computer-readable medium storing computer-executable instructions for a metaverse controller comprising one or more processors operatively coupled to one or more memories, the computer-executable instructions comprising one or more instructions instructing the one or more processors to:
determine a user condition based on biometrics of a user sensed by one or more biometric sensors; and
control one or more metaverse outputs of a metaverse presentation based on the user condition, the metaverse presentation being presented to the user, the metaverse outputs comprising any one or more of a visual output, an audio output, and a haptic output, and the metaverse presentation comprising a presentation that incorporates extended reality (XR),
wherein in determining the user condition comprises, the one or more instructions instruct the one or more processors to:
determine whether the biometrics are at or above a yellow condition threshold;
determine that the user condition is in a yellow condition upon determining that the biometrics are at or above the yellow condition threshold; and
determine that the user condition is in a green condition upon determining that the biometrics are below the yellow condition threshold,
wherein in controlling the one or more metaverse outputs, the one or more instructions instruct the one or more processors to:
provide a normal metaverse presentation upon the user condition being determined to be in the green condition; and
provide a cautionary metaverse presentation different from the normal metaverse presentation upon the user condition being determined to be in the yellow condition, and
wherein an amount of differentiation between the cautionary metaverse presentation and the normal metaverse presentation corresponds to a duration the user condition remains in the yellow condition.

* * * * *